United States Patent [19]  [11] Patent Number: 4,490,364
Rivier et al.  [45] Date of Patent: Dec. 25, 1984

[54] CCK AGONISTS II

[75] Inventors: Jean E. F. Rivier, La Jolla, Calif.; Botond Penke, Budapest, Hungary

[73] Assignee: The Salk Institute for Biological Studies, San Diego, Calif.

[21] Appl. No.: 522,846

[22] Filed: Aug. 12, 1983

Related U.S. Application Data

[63] Continuation-in-part of Ser. No. 496,455, May 20, 1983.

[51] Int. Cl.³ .................... A61K 37/00; C07C 103/52
[52] U.S. Cl. ............................ 424/177; 260/112.5 R; 260/112.5 LH
[58] Field of Search .............. 260/112.5 R, 112.5 LH; 424/177

[56] References Cited

U.S. PATENT DOCUMENTS 4,330,466  5/1982  Yanaihara et al. ........... 260/112.5 R
4,351,829  9/1982  Zetler et al. ................ 260/112.5 R Primary Examiner—Delbert R. Phillips
Attorney, Agent, or Firm—Fitch, Even, Tabin & Flannery

[57] ABSTRACT

Analogs of CCK(1-8) having dissociated activity with respect to stimulating the contraction of the gall bladder and arresting the secretion of gastric acid. Various analogs also exhibit improved anticonvulsive potency. The peptides are characterized by the following formula:

$$X-R_0-R_1-Tyr(Y)-R_3-R_4-Trp-R_6-R_7-R_8-NHQ$$

wherein X is H, Suc, Ac, Oxa, Mal, Glt, Prp, Prl or Acr; $R_0$ is Gln, pGlu, Cys, Tyr, Tyr(OCH$_3$), des—NH$_2$—Tyr or des$R_0$; $R_1$ is Asp, Tyr(OH or SE), Ser(OH or SE), Hyp(OH or SE), Thr(OH or SE), Cys, Tyr(OCH$_3$) or des$R_1$; Y is OH or SE; $R_3$ is Met, Nva or Nle; $R_4$ is Gly, D—Cys or D—Ala; $R_6$ is Met, Nva or Nle; $R_7$ is Asp, Ser(SE), Thr(SE) or Hyp(SE); $R_8$ is Phe or Tyr(OCH$_3$); and Q is lower alkyl, fluoro lower alkyl or hydrogen; provided that when $R_3$ and $R_6$ are Met and $R_7$ is Asp then $R_4$ is D—Ala. A pharmaceutically acceptable salt thereof may also be employed.

31 Claims, No Drawings

CCK AGONISTS II

This invention was made with Government support under Grant No. AM-26741 awarded by the National Institutes of Health. The Government has certain rights in this invention.

This application is a continuation-in-part of our earlier application Ser. No. 496,455 filed May 20, 1983.

The present invention relates to peptides containing residues of sulfated hydroxy amino acids and more particularly to CCK analogs.

BACKGROUND OF THE INVENTION

Ivy and Oddberg [*Amer. J. Physiol.* 86, 599 (1928)] in 1928 isolated from the mucous membrane of intestines a substance which caused the contraction of the gall-bladder and which they called "cholecystokinin". Harper and Raper [*J. Physiol.* 102, 115 (1943)] later described a substance called by these authors "pancreozymin", which was isolated from extracts of intestinal mucous membranes and which increased the enzyme secretion of the pancreas. Mutt and Jorpes [*Acta Chem. Scand.* 18, 2408 (1964)] have shown that both biological effects are caused by the same substance, a hormone called by these authors "cholecystokinin-pancreozymin". The same authors have also determined the amino acid sequence of this hormone [*Biochem. J.* 125, 678 (1971)]: Lys—Ala—Pro—Ser—Gly—Arg—Val—Ser—Met—Ile—Lys—Asn—Leu—Gln—Ser—Leu—Asp—Pro—Ser—His—Arg—Ile—Ser—Asp—Arg—Asp—Tyr($SO_3H$)—Met—Gly—Trp—Met—Asp—Phe—$NH_2$. Ondetti and Pluscec [*J. Am. Chem. Soc.* 92, 195(1970); *J. Med. Chem.* 13, 349 (1970)] synthesized the sulfate ester of C-terminal octapeptide amide of cholecystokinin-pancreozymin, hereinafter CCK(1-8), and a series of analogous compounds, and found that the octapeptide amide sulfate ester as well as some analogous compounds have a considerably higher activity than the complete molecule of cholecystokinin-pancreozymin.

This sulfate ester octapeptide amide, when administered in doses of about 1.0–6.0 μg/kg. of body weight, is a useful diagnostic means for the examination of the contraction of the gall bladder and to control pancreatic secretion. When administered i.v. at low dosages, the peptide exhibits some gastrinic activity in causing secretion of gastric acid. More recent investigations have also revealed that the octapeptide amide sulfate ester exerts a strong relaxing action on the muscle sphincter Oddii; thus, this compound can be used with good results to alleviate the spasms occurring after gall-bladder operations [see M. A. Ondetti, B. Rubin, S. Engel: *J. Amer. Digestive Diseases* 15, 149 (1970)]. CCK has also been found to serve as a brain neurotransmitter and to regulate appetite and have other effects upon the central nervous system, as described in detail in a review by Morley, J. E., *Life Sciences*, 30, 479–493 (1982).

Investigators have sought analogs of these octapeptides having improved therapeutic properties.

SUMMARY OF THE INVENTION

Analogs of CCK(1-8) have been found which exhibit improved potency with respect to CCK-activity relating to contraction of the gall bladder while exhibiting either reduced or negligible gastrinic activity. Moreover, various of the analogs exhibit improved anticonvulsive potency effect. The peptides of the invention are characterized by the following formula:

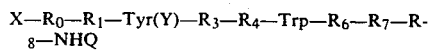

wherein X is H, Suc, Ac, Oxa, Mal, Glt, Prp, Prl or Acr; $R_0$ is Gln, pGlu, Cys, Tyr, Tyr($OCH_3$), des—$NH_2$—Tyr or des$R_0$; $R_1$ is Asp, Tyr(OH or SE), Ser(OH or SE), Hyp(OH or SE), Thr(OH or SE), Cys, Tyr($OCH_3$) or des$R_1$; Y is OH or SE; $R_3$ is Met, Nva or Nle; $R_4$ is Gly, D—Cys or D—Ala; $R_6$ is Met, Nva or Nle; $R_7$ is Asp, Ser(SE), Thr(SE) or Hyp(SE); $R_8$ is Phe or Tyr($OCH_3$); and Q is lower alkyl, fluoro lower alkyl or hydrogen; provided that when $R_3$ and $R_6$ are Met and $R_7$ is Asp then $R_4$ is D—Ala.

DETAILED DESCRIPTION OF PREFERRED EMBODIMENTS

Peptides are compounds which contain two or more amino acids in which the carboxyl group of one acid is linked to the amino group of the other acid. The formula for a peptide is represented in accordance with conventional representation of peptides where the amino terminus appears to the left and the carboxyl terminus to the right. The position of the amino acid residue is identified by numbering the amino acid residues from left to right. In the case of CCK(1-8), the hydroxyl portion of the carboxyl group of has been replaced with an amino group ($NH_2$) and is so indicated; if there is no indication, it should be assumed the OH group is present. Likewise, if there is no indication at the N-terminus, the α-amino group is unsubstituted. The abbreviations for the individual amino acid residues above are conventional and are based on the trivial name of the amino acid, e.g., Met is methionine, Nle is norleucine, Nva is norvaline, Tyr is tyrosine, Trp is tryptophan, Gly is glycine, Asp is aspartic acid, Ser is serine, Hyp is hydroxyproline, Phe is phenylalanine, Thr is threonine, Cys is cysteine and Ala is alanine. Except for glycine, the amino acids of the peptides described hereinafter should be understood to be of the L-configuration unless the D-isomer is specified. By Ac is meant acetyl, by Acr is meant acrylyl, by Oxa is meant oxalyl, by Mal is meant maleyl, by Glt is meant glutaryl, by Prp is meant propionyl, by Prl is meant propiolyl and by Suc is meant succinyl. By SE is meant the sulfate ester ($OSO_3H$) or the salt thereof with an alkali base, e.g. ($OSO_3Na$) or the salt thereof with an organic base, e.g. ($OSO_3^{31}HNEt_3^+$ and $OSO_3^{31}HC_5H_5^+$).

The invention relates to heptapeptide, octapeptide, nonapeptide and other N-extended analogs of CCK(1-8). In the heptapeptide, the amino acid residue in the 1-position is deleted and preferably replaced with an acyl group. More particularly, the present invention relates to such CCK analogs wherein a substitution has been made for Gly in the 4-position, for Met in the 3- or 6-position or for Asp in the 7-position. Moreover, tyrosine in the 2-position may have the hydroxyl group on the phenolic side chain either in free hydroxyl form or sulfated. The 7-position substitutents are sulfated esters of hydroxy-containing amino acids. Any of the sulfate esters may be present in the form of the sodium or other alkali or organic basic salt thereof without affecting pharmaceutical activity. When Tyr is employed in the 0-or 1-position, the α-amino group may be eliminated, i.e. des—$NH_2$—Tyr. By either substituting Tyr or preferably Tyr(OCH$_3$) for Phe in the 8-position or for Asp in the 1-position or by adding such a residue in the 0-position, the residue can be radioiodinated and used as a tracer.

The CCK analogs which contain Tyr or Tyr(OCH$_3$) in the 0-, 1- or 8-position have the advantage that they can be easily labelled with radioactive iodine, $^{125}$I or $^{131}$I. The measurement of the CCK-8 concentration in human blood plasma or serum has been a serious problem until now. Because the normal level of CCK-8 (as that of other peptide hormones) is very low, the method of choice for measuring CCK would be by radioimmunoassay (RIA). This method needs radioiodinated peptide hormones of high specific radioactivity (~1500-2000 Ci (mmol)) and of high purity. Unfortunately, CCK cannot be radioiodinated easily because the sulfate ester on the Tyr does not allow the introduction of a large iodine atom into the aromatic ring. Besides, oxidation of the two Met residues during the iodination can give a very complex reaction mixture, purification of which is extremely difficult. However, when the Met residues are replaced with the sterically very similar Nle, which is stable during the iodination procedure, this problem disappears. Therefore radioiodination of the peptides H—Tyr—Asp—Tyr(OSO$_3$Na)—Nle—Gly—Trp—Nle—Asp—Phe—NH$_2$ or H—Asp—Tyr(OSO$_3$Na)—Nle—Gly—Trp—Nle—Hyp(OSO$_3$Na)—Tyr(OCH$_3$)—NH$_2$, for example, is quite easy and gives pure iodinated peptides of high specific radioactivity. Radioiodination can be performed by the known method of Hunter and Greenwood [*Chem. Rev.* 78, 65, 1978] using Na$^{125}$I and Chloramin-T as an oxidation reagent. Specific antibodies used in RIA will recognize these iodinated peptides as CCK-8, and therefore they can serve as ideal tracers for measurement of CCK-8 concentration by RIA.

More specifically, the compounds of the present invention are peptides having the following formula:

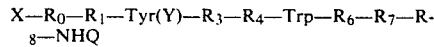

wherein X is H, Suc, Ac, Oxa, Mal, Glt, Prp, Prl or Acr; R$_0$ is Gln, pGlu, Cys, Tyr, Tyr(OCH$_3$), des—NH$_2$—Tyr or desR$_0$; R$_1$ is Asp, Tyr(OH or SE), Ser(OH or SE), Hyp(OH or SE), Thr(OH or SE), Cys, Tyr(OCH$_3$) or desR$_1$; Y is OH or SE; R$_3$ is Met or Nle; R$_4$ is Gly, D—Cys or D—Ala; R$_6$ is Met or Nle; R$_7$ is Asp, Ser(SE), Thr(SE) or Hyp(SE); R$_8$ is Phe or Tyr(OCH$_3$); and Q is lower alkyl, fluoro lower alkyl or hydrogen; provided that when R$_3$ and R$_6$ are Met and R$_7$ is Asp then R$_4$ is D—Ala or a pharmaceutically acceptable salt thereof.

As used herein, the term "pharmaceutically acceptable salts" refer to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, alginic acid, polyglutamic acid, naphthalenesulfonic acids, naphthalenedisulfonic acids and polygalacturonic acid; (b) salts with polyvalent metal cations, such as zinc, calcium, bismuth, barium, magnesium, aluminum, copper, cobalt, nickel, cadmium, and the like; or with an organic cation formed from N,N'-dibenzylethylenediamine or ethylenediamine; combinations of (a) and (b), e.g., a zinc tannate salt and the like.

Preferred compounds of the invention are those wherein X is Ac or Suc when R$_0$ and R$_1$ are deleted, R$_3$ is Met or Nle, R$_4$ is Gly or D—Ala, R$_6$ is Met or Nle, R$_7$ is Ser(OSO$_3$H), Thr(OSO$_3$H) or Hyp(OSO$_3$H), R$_8$ is Phe or Tyr(OCH$_3$) and Q is H or CH$_3$. Particularly preferred compounds are:

[Tyr$^2$,Ser(OSO$_3$Na)$^7$]—Ac—CCK(2-8); [Ser(OSO$_3$Na)$^7$]—Ac—CCK(2-8); [Tyr$^2$,Thr(OSO$_3$Na)$^7$]—Ac—CCK(2-8); [Tyr(OCH$_3$)$^1$, Ser(OSO$_3$Na)$^7$]—Ac—CCK(1-8); [Tyr$^2$, Hyp(OSO$_3$Na)$^7$]Ac—CCK(2-8); [Thr(OSO$_3$Na)$^7$]—Ac—CCK(2-8); [Hyp(OSO$_3$Na)$^7$]—Ac—CCK(2-8); [D—Ala$^4$]—Ac—CCK(2-8); [D—Ala$^4$, Hyp(OSO$_3$Na)$^7$]—Ac—CCK(2-8); [Nle$^{3,6}$,D—Ala$^4$,Hyp(OSO$_3$Na)$^7$]—Suc—CCK(2-8); [Nle$^{3,6}$,D—Ala$^4$,Hyp(OSO$_3$Na)$^7$]—Ac—CCK(2-8); [Nle$^{3,6}$,Hyp(OSO$_3$Na)$^7$, Tyr(OCH$_3$)$^8$]—CCK(1-8); [Ser(OSO$_3$Na)$^1$, Nle$^{3,6}$, Hyp(OSO$_3$Na)$^7$]—CCK(1-8); [D—Ala$^4$, Thr(OSO$_3$Na)$^7$]—Ac—CCK(2-8); and [Nle$^{3,6}$,D—Ala$^4$, Hyp(OSO$_3$Na)$^7$]—Suc—CCK(2-8)—NHCH$_3$.

The peptides of the present invention can be synthesized by classical solution synthesis as generally described in U.S. Pat. Nos. 4,102,878 and 3,778,429. They may also be synthesized using solid-phase techniques on a chloromethylated resin, a methylbenzhydrylamine resin (MBHA) or a benzhydrylamine (BHA) resin. The solid-phase synthesis is conducted in a manner to stepwise add amino acids in the chain in the manner set forth in detail in U.S. Pat. No. 4,211,693. Side-chain protecting groups, as are well known in the art, are preferably added to Tyr and to either Asp or its hydroxy-containing substituent (depending upon the method of sulfation chosen) and to Cys or Gln if employed, and they may optionally be added to Trp and Met, before these amino acids are coupled to the chain being built upon the resin. Such a method provides the fully protected intermediate peptidoresin.

The intermediates of the resin may be represented as:

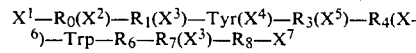

wherein

X$^1$ is an α-amino protecting group of the type known to be useful in the art in the stepwise synthesis of polypeptides and when X in the desired peptide composition is a particular acyl group, that group may be used as the protecting group. Among the classes of α-amino protecting groups covered by X$^1$ are (1) acyl-type protecting groups, such as formyl (For), trifluoroacetyl, phthalyl, p-toluenesulfonyl (Tos), benzoyl (Bz), benzensulfonyl, o-nitrophenylsulfenyl (Nps), tritylsulfenyl, o-nitrophenoxyacetyl, acrylyl (Acr), chloroacetyl, acetyl(Ac) and γ-chlorobutyryl; (2) aromatic urethan-type protecting groups, e.g., benzyloxycarbonyl(Z) and substituted benzyloxycarbonyl, such as p-chlorobenzyloxycarbonyl, p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred α-amino protecting group is Boc when X is hydrogen.

$X^2$ may be hydrogen or a protecting group for the phenolic hydroxyl group of Tyr, if Tyr is present, such as tetrahydropyranyl, tert-butyl, trityl, benzyl, benzyloxycarbonyl, 4-bromobenzyloxycarbonyl and 2,6-dichlorobenzyl(DCB), or a protecting group for the amido group of Gln, such as xanthyl(Xan), if Gln is present, or a protecting group for the sulfhydryl group of Cys, such as $X^4$, if Cys is present. 2,6-Dichlorobenzyl is preferred when Tyr is present; however when Tyr-($OCH_3$) is used, no additional protection is needed.

$X^3$ may be an ester-forming protecting group for the β-carboxyl group of Asp and is preferably selected from the group consisting of benzyl(OBzl), 2,6-dichlorobenzl, methyl, ethyl and t-butyl ester(OBut). OBzl is preferred when Asp is employed. Alternatively, when a hydroxy-containing amino acid that is not initially sulfated is substituted for Asp, $X^3$ may be a protecting group for the hydroxyl group, such as acetyl, benzoyl, tetrahydropyranyl, tert-butyl, trityl, benzyl and 2,6-dichlorobenzyl or one of the others specified with respect to $X_2$ if Tyr is present; benzyl is preferred for Ser, Thr and Hyp. Furthermore, if Cys is present, a protecting group such as $X^4$ may be used. $X^3$ may also be hydrogen, which means there is no side chain protecting group. $X^3$ may also be $SO_3H$ or $SO_3Na$ depending upon the particular synthesis employed.

$X^4$ may be hydrogen or a protecting group for the phenolic hydroxyl group of Tyr, if Tyr is protected, such as specified in respect of $X_2$; however $X^4$ may also be $SO_3H$ or $SO_3Na$ depending upon the particular synthesis employed.

$X^5$ may be a protecting group for the hydroxyl group when Thr is employed, as specified in respect of $X^3$. $X^5$ may be hydrogen, which means there is no side chain protecting group.

$X^6$ is hydrogen or a protecting group for the sulfhydryl group of Cys, such as benzyl(Bzl), substituted Bzl, e.g. 3,4-dimethyl benzyl, p-methoxybenzyl(MeOBzl), p-chlorobenzyl and p-nitrobenzyl, trityl, Z, substituted Z, thioethyl, acetamidomethyl(AF and Bz. MeOBzl is preferred.

$X^7$ is selected from the group consisting of O—$CH_2$—[resin support], NH—[resin support], $NCH_3$—[resin support], esters, NHQ and hydrazide.

The criterion for selecting side chain protecting groups is that the protecting group should be stable to the reagent under the reaction conditions selected for removing the α-amino protecting group at each step of the synthesis. The protecting group should not be split off under coupling conditions, and the protecting group should be removable upon completion of the synthesis of the desired amino acid sequence under reaction conditions that will not alter the peptide chain.

When the $X^7$ group is O—$CH_2$—[resin support], the ester moiety of one of the many functional groups of a polystyrene resin support is being represented. When the $X^7$ group is —NH—[resin support] or —$NCH_3$—[resin support], an amide or substituted-amide bond connects Phe or Tyr to a BHA resin or to an MBHA resin.

When X is an acyl group in the final formula, it may be possible to employ it as the $X^1$ protecting group for the α-amino group of amino acid which is to be present at the N-terminus by adding it before the coupling of this last amino acid to the peptide chain. However, a reaction is preferably carried out with the peptide on the resin (after deblocking the α-amino group while the side-chain groups remain protected), e.g. by reacting with acetic acid in the presence of dicyclohexyl carbodiimide (DCC) or preferably with acetic anhydride or by another suitable reaction as known in the art.

The fully protected peptide can be cleaved from a chloromethylated resin support by ammonolysis, as is well known in the art, to yield the fully protected amide intermediate. Deprotection of the peptide, as well as cleavage of the peptide from a benzhydrylamine resin, can take place at 0° C. with hydrofluoric acid (HF). Anisole is preferably added to the peptide prior to treatment with HF. After the removal of HF under vacuum, the cleaved, deprotected peptide is conveniently treated with ether, decanted, taken-up in dilute acetic acid and lyophilized.

Purification of the peptide is effected by ion exchange chromatography on a CMC column, followed by partition chromatography using the elution system n-butanol; 0.1 M acetic acid (1:1 volume ratio) on a column packed with Sephadex G-25, or by using HPLC, as known in the art.

Thus, there is also provided a process for the manufacture of compounds defined by the formula:

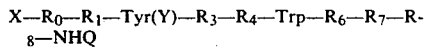

wherein X is H, Suc, Ac, Oxa, Mal, Glt, Prp, Prl or Acr; $R_0$ is Gln, pGlu, Cys, Tyr, Tyr($OCH_3$), des—$NH_2$—Tyr or des$R_0$; $R_1$ is Asp, Tyr(OH or SE), Ser(OH or SE), Hyp(OH or SE), Thr(OH or SE), Cys, Tyr($OCH_3$) or des$R_1$; Y is OH or SE; $R_3$ is Met or Nle; $R_4$ is Gly, D—Cys or D—Ala; $R_6$ is Met or Nle; $R_7$ is Asp, Ser(SE), Thr(SE) or Hyp(SE); $R_8$ is Phe or Tyr($OCH_3$); and Q is lower alkyl, fluoro lower alkyl or hydrogen; provided that when $R_3$ and $R_6$ are Met and $R_7$ is Asp then $R_4$ is D—Ala or a pharmaceutically acceptable salt thereof comprising (a) forming an intermediate peptide having at least one protective group and the formula:

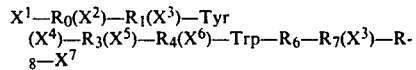

wherein $X^1$ is H or an α-amino protecting group; $X^2$ is H,Y or a side chain protecting group; $X^3$ is hydrogen or a side chain protecting group; $X^4$ is H,Y or a protecting group for the phenolic hydroxyl group; $X^5$ is H or an hydroxyl group protecting group; $X^6$ is H or a sulfhydrl group protecting group; and $X^7$ is selected from the group consisting of O—$CH_2$—[resin support], NH—[resin support], —$NCH_3$—[resin support], esters, NHQ and hydrazide; (b) splitting the protective group or groups or anchoring bond from said intermediate peptide, and (c) if desired, converting the resulting peptide into a pharmaceutically acceptable salt thereof.

As indicated above, the peptides may be made by any suitable method of synthesis or may be made using recombinant DNA technology. Ondetti et al. described a process for the preparation of the octapeptide amide sulfate ester [J. Am. Chem. Soc. 92, 195 (1970)]. The protected peptide amide and the intermediate compounds used in such a synthesis are prepared by known methods of peptide chemistry. Then the tyrosine residue can be sulfated in known manner by treatment with a complex of pyridine and sulfur trioxide, and finally the protective groups are removed by acidolysis with trifluoroacetic acid. Yields about 30 percent can be obtained with this process.

Preferably, the peptides are prepared by the methods described in detail in our copending U.S. patent application Ser. No. 439,312, filed Oct. 4, 1982. The sulfation of a hydroxy amino acid or of a residue of such an amino acid in a peptide is carried out by reaction with a reagent which is a tertiary ammonium salt of acetylsulfuric acid having the formula: $[CH_3COOSO_3]^-[RH]^+$ wherein R is triethylamine, ethyldiisopropylamine, pyridine, N-methylmorpholine or 4-N,N-dimethylaminopyridine. This general method is suitable for synthesis of sulfate esters of hydroxy amino acids as such, or within a peptide or a peptide hydrazide sequence, without any substantial side reactions, while other labile side-chain groups are either protected or unprotected. The reaction is preferably carried out at room temperature and atmospheric pressure by allowing the reactants to stand for about 2–5 days in an appropriate mutual solvent. Other equivalent reaction conditions may be used.

The reagent can be easily synthesized by reacting a mixture of acetic anhydride and an appropriate tertiary amine, e.g., triethylamine, diisopropylethylamine, N-methylmorpholine, pyridine, 4-N,N-dimethylaminopyridine, etc., with sulfuric acid at 0° C. The tertiary ammonium salts of acetylsulfuric acid are stable, crystalline compounds which react only with the alcoholic or the phenolic hydroxyl group of hydroxyamino acids (e.g., serine, threonine, hydroxyproline and tyrosine) and which do not readily react with free amino, guanido, imidazole, hydrazide, sulfhydryl or thioether groups that may be present either in a free amino acid or in side chains in peptides.

The reaction can be carried out with other labile side-chain groups either protected or unprotected in amino acids and peptides, and residue containing the unprotected hydroxyl group which reacts may be anywhere in the chain, i.e., it may be at either end of a peptide or it may have a peptide fragment at both ends thereof. The α-amino group of the free amino acid at the N-terminus of the peptide may be unprotected, acylated or protected by tert-butyloxycarbonyl(BOC), fluorenylmethyloxy-carbonyl(FMOC) or benzyloxycarbonyl(Z). If acylated, the acyl group would generally not have more than about 12 carbon atoms. Likewise, the carboxyl group of the amino acid, or the C-terminus of the peptide, may have substantially any of the usual groups attached thereto, such as OH, $OCH_3$, OEt, OBzl, $NH_2$ and $N_2H_3$. They may also have other groups useful in active-ester coupling. If the peptide is made by solid-phase synthesis, the sulfation reaction may be carried out while the peptide is attached to a resin or following cleavage therefrom.

The main advantages of the use of acetyl sulfuric acid tertiary ammonium salts for sulfation of amino acids and peptides are easy synthesis of the reagents and selective reaction with the hydroxyl groups without significant side reactions, hence high yields and high purity of the sulfate esters being synthesized.

In general, the sulfate-ester-containing peptides of the invention are prepared by either: (a) introducing the sulfate ester group(s), using the acetylsulfuric acid reagent, directly into a synthetic peptide containing a hydroxyamino acid residue; or (b) introducing the appropriate N-protected hydroxyamino acid sulfate ester into the peptide chain during the stepwise synthesis of the peptide.

An automatic peptide synthesizer (Beckman, Model 990B) is used for the solid-phase synthesis of peptides. The standard cycle of coupling onto about 10 g. of resin, acetylation of uncoupled amino groups and deblocking is as follows:

| STEP | REAGENTS AND OPERATIONS | MIX TIMES MIN. |
|---|---|---|
| 1 | $CH_2Cl_2$ wash-80 ml. (2 times) | 3 |
| 2 | Methanol(MeOH) wash-30 ml. (2 times) | 3 |
| 3 | $CH_2Cl_2$ wash-80 ml. (3 times) | 3 |
| 4 | 50 percent TFA plus 5 percent 1,2-ethane-dithiol in $CH_2Cl_2$—70 ml. (2 times) | 10 |
| 5 | $CH_2Cl_2$ wash-80 ml. (2 times) | 3 |
| 6 | TEA 12.5 percent in $CH_2Cl_2$—70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30–300 |
| 10 | MeOH wash-40 ml. (2 times) | 3 |
| 11 | $(CH_3CO)_2O$ (3 molar) in $CH_2Cl_2$—70 ml. (1 time) | 3 |
| 12 | MeOH wash-30 ml. (2 times) | 3 |
| 13 | $CH_2Cl_2$ wash-80 ml. (2 times) | 3 |

The HF cleavage of the peptide from the resin and deprotection is performed in nonaqueous medium at 0° C. for 45 minutes. Peptide purity control is checked by reverse phase HPLC. The preparative HPLC purification is achieved on Waters Associates Prep LC500 using custom-made cartridges. Optical rotations are measured on a Perkin-Elmer spectropolarimeter. Peptide hydrolysis is performed in 4 M methane sulfonic acid containing 0.2% tryptamine, using hydrolysis time of 24 hours at 110° C. in sealed ampules under high vacuum. For amino acid analysis, the hydrolysates are neutralized and loaded to the column of Beckman automatic amino acid analyzer Model 121M. Melting points are not corrected.

The following Examples are exemplary of the formation of the reagents and the reactions thereof with amino acids and with peptides:

EXAMPLE I

Acetylsulfuric acid pyridinium salt

A mixture of 30 ml of acetic anhydride and 8.05 ml (0.1 mole) of pyridine is cooled to 0° C., and 5.4 ml of conc. $H_2SO_4$ is added dropwise at 0° C. under stirring. After 10 minutes, the crystals are filtered, washed with diethyl ether and dried under vacuum over $P_2O_5$ and KOH. Yield: 18.4 g (84%). IR: 1050 cm$^{-1}$ sharp band, characteristic for sulfates and sulfate esters. Decomposes above 75° C., very hygroscopic. MW: 219.2 ($C_7H_9O_5NS$).

EXAMPLE II

Tert. butyloxycarbonyl tyrosine sulfate ester sodium salt 11.24 g. (0.04 moles) of Boc—Tyr is dissolved in 100 ml of pyridine, and 13.2 g (0.06 moles) of acetylsulfuric acid pyridinium salt is added under stirring. After standing overnight at 20° C., the clear solution is evaporated to dryness. The oily residue is dissolved in 300 ml of water, and the pH is adjusted with 1 N NaOH to 8.0.

The liberated pyridine is extracted 3 times with diethyl ether. The pH of the aqueous solution is readjusted with 1N $H_2SO_4$ to 3.5 and lyophilized. To the fluffy white powder, 100 ml of $CH_2Cl_2$ is added; the insoluble material ($Na_2SO_4$) is centrifuged and discarded. 200 ml of ether is added to the dichloromethane solution, and the material precipitates as white crystals. After filtering, Boc—Tyr($OSO_3Na$) is washed with ether and dried under vacuum. Yield: 14.2 g(93%); MW: 383.5; IR: sharp band at 1050 $cm^{-1}$. $[\alpha]_D^{20} = +4.7°$ (c=1,$H_2O$).

EXAMPLE III

Tert. butyloxycarbonyl 3—hydroxyproline sulfate ester, sodium salt

Boc—Hyp($OSO_3Na$) is synthesized from 10.0 g. (0.043 moles) of Boc—3—Hyp and 14.3 g (0.065 moles) of acetylsulfuric acid pyridinium salt as generally described in Example II. Yield: 13 g(82%); IR: sharp band at 1080 $cm^{-1}$.

EXAMPLE IV

Ac—[D—Ala$^4$] Cholecystokinin (2-8) heptapeptide

Ac—Tyr($OSO_3Na$)—Met—D—Ala—Trp—Met—Asp—Phe—$NH_2$ is prepared by solid-phase synthesis as follows: Boc—Tyr—Met—D—Ala—Trp—Met—Asp—Phe—$NH_2$ is built up in a stepwise manner using a methylbenzhydrylamino(MBHA) resin as polymer support, using BOC-protected amino acids and using DCC as the coupling reagent. The phenol hydroxyl of Tyr is protected with the 2,6-dichlorobenzyl group during the peptide synthesis.

Boc—Phe (1.59 g: 6 mmoles) is coupled onto an MBHA resin (6.0 g: 2.4 mmoles) at a free amino group on the resin. The following 6 residues are sequentially attached thereafter using the standard synthesis scheme shown in Table I: Boc-Asp(OBzl) 1.94 g (6 mmoles); Boc—Met 1.5 g (6 mmoles); Boc—Trp 1.83 g (6 mmoles); Boc—D—Ala 1.14 g (6 mmoles); Boc—Met 1.5 g (6 mmoles); and Boc—Tyr(2,6 dichloro Bzl) 2.64 g (6 mmoles). Each of the amino acids is dissolved in 45 ml of $CH_2Cl_2$, except for Boc—Trp, which is dissolved in $CH_2Cl_2$ containing 10% DMF. 6 mmoles of dicyclohexylcarbodiimide (DCC) dissolved in $CH_2Cl_2$ is used for each coupling.

After the last coupling step, the Boc protection for Tyr is removed, and acetylation is performed on the resin by treatment with acetyl anhydride, the heptapeptidyl-resin is dried in vacuo, and the CCK-heptapeptide is cleaved from the polymer support with HF(90 ml), 10 ml of anisole and 1 ml of methylethyl-sulfide(MES) at 0° C., which also removes the side-chain protecting groups. The heptapeptide is dissolved in 50 ml of DMF and filtered to eliminate the resin. It is then precipitated with 50 ml of ethyl ether, yielding 2.0 g. of a white solid material.

After drying, it is dissolved in DMF (10 ml) and pyridine (8 ml) to which acetylsulfuric acid pyridinium salt 1.5 g (7 mmoles) is added. After standing for 3 days at 20° C., it is neutralized with acetic acid and evaporated to dryness. The resulting yellow oil is triturated with 30 ml 0.1N HCl at 0° C., and the peptide which precipitates as a white solid is isolated by centrifugation. The CCK-heptapeptide sulfate ester obtained is dissolved in 30 ml $CH_3OH$ and 470 ml of $H_2O$, and pH is adjusted to about 6.5 using NaOH. The insoluble colloidal material is filtered off on cellite, and the peptide is purified by preparative reverse phase HPLC using a gradient of acetonitrile in 0.1 M $NH_4$-acetate (pH=6.5).

555 mg (0.44 mmoles) of cholecystokinin heptapeptide sodium salt (Ac—Tyr($OSO_3Na$)—Met—D—Ala—Trp—Met—Asp—Phe—$NH_2$) is isolated from the aqueous solution after two lyophilizations. Amino acid analysis is consistent with expected values, and a single peak is shown on HPLC. IR: sharp band at 1050 $cm^{-1}$; $[\alpha]_D^{20} = -15.0°$(c=2,DMF).

EXAMPLE V

[Hyp($OSO_3Na$)$^7$]—Ac—CCK(2-8)

The N-protected hydroxyamino acid sulfate esters are used directly in the stepwise build-up of peptides. The heptapeptide is synthesized on 2.0 g (1.1 mmole) benzhydrylamine resin using the general process described earlier in Example IV. Introduction of the Hyp- and the Tyr-sulfate ester moieties into the molecule is accomplished using Boc-protected sulfate ester sodium salts.

The following protected amino acids are used: Boc—Gly (0.53 g, 3 mmoles); Boc-Phe (0.80 g, 3 mmoles); Boc—Met (1.50 g, 6 mmoles); Boc-Tyr-($OSO_3Na$) (1.15 g, 3 mmoles); Boc—Hyp($OSO_3Na$) (3.1 g, 10 mmoles); Boc—Trp (0.92 g, 3 mmoles). All couplings are mediated by DCC. Boc—Hyp($OSO_3Na$) and Boc—Tyr($OSO_3Na$) are each coupled in the presence of 3 mmoles of pentafluorophenol in 30 ml $CH_2Cl_2$. Acetylation is then performed on the resin by treatment with acetic anhydride. The peptide is cleaved from the resin and deprotected with 50 ml of HF containing 5 ml of anisole (40 minutes at 0° C.). The crude heptapeptide (1.0 g) is dissolved in 500 ml of $H_2O$, and the pH is adjusted to 7.0 with NaOH. The peptide is purified by reverse phase HPLC using a gradient of $CH_3CN$ in triethylammonium phosphate buffer, pH 2.25, and by desalting using 0.1% TFA/$CH_3CN$ on preparative HPLC. 561 mg of the pure peptide is isolated after lyophilization. Amino acid analysis is consistent with expected values. $[\alpha]_D^{20} = -18.2°$(C=2, DMF).

By substituting Boc—D—Ala for Boc—Gly and Boc—Thr for Boc—Hyp, the corresponding double-substituted CCK(2-8) analog is created. [D—Ala$^4$, Thr($OSO_3Na$)$^7$]—Ac—CCK(2-8) is considered to have particular efficacy.

EXAMPLE VI

Because amino acids containing alcoholic hydroxyl groups react faster with the reagent than does the phenolic hydroxyl of Tyr, the selective sulfation of a Ser-residue may be effected in a peptide containing both Ser and Tyr. Longer reaction time will lead to sulfation of some Tyr. Two analogs of cholecystokinin, i.e., [Tyr$^2$, Ser($OSO_3Na$)$^7$]—acetyl—CCK(2-8) and [Tyr($OSO_3Na$)$^2$, Ser($OSO_3Na$)$^7$]—acetyl—CCK(2-8), are synthesized as follows: The acetyl heptapeptide Ac—Tyr—Met—Gly—Trp—Met—Ser—Phe is assembled on an MBHA resin using BOC for N-protection. Tyr is protected with 2,6-dichlorobenzyl ether and Ser with Bzl. Acetylation of the heptapeptide is performed on the resin by reacting the heptapeptidyl-resin with acetic anhydride in $CH_2Cl_2$. After HF-cleavage and deprotection (in the presence of 10% anisole and 1% MES as scavengers) to produce the acetyl heptapeptide amide, it is purified by precipitation from DMF with ethyl ether and dissolved in DMF-pyridine 2:1 (v/v). A 5-fold excess of acetylsulfuric acid pyridinium salt is then added. After standing for 5 days at 20° C., the reaction mixture is diluted with water, and the pH of the solution is adjusted to 7.5 with NaOH. The two peptides, Ac—Tyr(OSO$_3$Na)—Met—Gly—Trp—Met—Ser(OSO$_3$Na)—Phe—NH$_2$ and Ac—Tyr—Met—Gly—Trp—Met—Ser(OSO$_3$Na)—Phe—NH$_2$, in a ratio of about 1:1, separate on a reverse phase preparative HPLC column. The more hydrophilic disulfate ester has a shorter retention time and is easily separated from the less hydrophylic monosulfate ester and from the unreacted starting material.

Analogs of the Ac—CCK(2-8) heptapeptide containing sulfate ester of Thr in the 7-position instead of Ser are synthesized in the same way to obtain [Tyr$^2$, Thr(OSO$_3$Na)$^7$]—Ac—CCK(2-8) and [Tyr(OSO$_3$Na)$^2$, Thr(OSO$_3$Na)$^7$]—Ac—CCK(2-8) in a ratio of about 1:1.

EXAMPLE VII

[Nle$^{3,6}$, Hyp(OSO$_3$Na)$^7$, Tyr(OCH$_3$)$^8$]—Ac—CCK(1-8)

The N-protected hydroxyproline sulfate ester is used directly in the stepwise build-up of this peptide. The octapeptide is synthesized on 2.0 g (1.1 mmole) benzhydrylamine resin using the general process described earlier in Example IV. Introduction of the Hyp- and the Tyr-sulfate ester moieties into the molecule is accomplished using Boc-protected sulfate ester sodium salts.

The following protected amino acids are used: Boc—Asp(OBut) (0.87 g, 3 mmoles); Boc—Gly (0.53 g, 3 mmoles); Boc—Tyr(OCH$_3$) (0.89 g, 3 mmoles); Boc—Nle (1.50 g, 6 mmoles); Boc—Tyr(OSO$_3$Na) (1.15 g, 3 mmoles); Boc—Hyp(OSO$_3$Na) (3.1 g, 10 mmoles); Boc—Trp (0.92 g, 3 mmoles). All couplings are mediated by DCC. Boc—Hyp(OSO$_3$Na) and Boc—Tyr(OSO$_3$Na) are each coupled in the presence of 3 mmoles of pentafluorophenol in 30 ml CH$_2$Cl$_2$. The peptide is cleaved from the resin and deprotected with 50 ml of HF containing 5 ml of anisole (40 minutes at 0° C.). The crude octapeptide (1.0 g) is dissolved in 500 ml of H$_2$O, and the pH is adjusted to 7.0 with NaOH. The peptide is purified by reverse phase HPLC using a gradient of CH$_3$CN in triethylammonium phosphate buffer, pH 2.25, and by desalting using 0.1% TFA/CH$_3$CN on preparative HPLC. 301 mg of the pure peptide is isolated after lyophilization. Amino acid analysis is consistent with expected values.

EXAMPLE VIII

[Tyr$^0$, Nle$^{3,6}$]-CCK(1-8)

The nonapeptide is synthesized on 2.0 g (1.1 mmole) benzhydrylamine resin using the general process described earlier in Example IV. Introduction of the Tyr-sulfate ester moiety into the molecule is accomplished using the Boc-protected sulfate ester sodium salt.

The following protected amino acids are used: Boc—Asp(OBzl) (1.85 g, 6 mmoles); Boc—Gly (0.53 g, 3 mmoles); Boc—Phe (0.80 g, 3 mmoles); Boc—Nle (1.50 g, 6 mmoles); Boc—Tyr(OSO$_3$Na) (1.15 g, 3 mmoles); Boc—Tyr(DCB) (1.32 g, 3 mmoles); Boc—Trp (0.92 g, 3 mmoles). All couplings are mediated by DCC. Boc—Tyr(OSO$_3$Na) is coupled in the presence of 3 mmoles of pentafluorophenol in 30 ml CH$_2$Cl$_2$. The peptide is cleaved from the resin and deprotected with 50 ml of HF containing 5 ml of anisole (40 minutes at 0° C.). The crude nonapeptide (0.9 g) is dissolved in 500 ml of H$_2$O, and the pH is adjusted to 7.0 with NaOH. The peptide is purified by reverse phase HPLC using a gradient of CH$_3$CN in triethylammonium phosphate buffer, pH 2.25, and by desalting using 0.1% TFA/CH$_3$CN on preparative HPLC. 250 mg of the pure peptide is isolated after lyophilization. Amino acid analysis is consistent with expected values.

To determine the effectiveness of the various synthetic peptides, they are tested for their ability to stimulate the contraction of the gall bladder, for gastrinic activity in the stomach and for their anticonvulsive effect. Certain well known tests are carried out, and the results are measured and compared to the activity of CCK(1-8). Some of the results are given as a percentage relative to the activity of CCK(1-8). The ability to stimulate the contraction of the gall bladder is measured using a modified method of Amer and Becvar, described in *J. Endocrinology*, 43, 637 (1969) and employing isolated strips of rabbit gall bladder. Gastrinic activities are measured on perfused rat stomach by conductrometric titration of HCl liberated as a result of iv administration of the equivalent amount of test solution and compared to the administration of comparable amounts of pentagastrin.

The anticonvulsive effect is measured by the method as generally described in *The European J. of Pharm.*, 65, 297 (1980). More specifically, a mouse is first injected parenterally with the peptide being tested with a single dose equal to about 0.8 micromoles per kilogram of body weight. Thereafter, picrotoxin is injected i.p. in an amount equal to about six micrograms per kg of body weight. The parameters that are measured: time until first tremor, time until first clonic seizure, time until first tonic seizure and time of latentia until death, measured from the time of injection of the picrotoxin.

The test results are set forth in Tables I and II hereinafter:

TABLE I

| CCK Analog | CCK-activity % /CCK (1-8) 100%/ | gastrinic activity % /Pentagastrin 100%/ |
| --- | --- | --- |
| [Ser(OSO$_3$Na)$^7$]-Ac-CCK (2-8) | 190 | 0 |
| [Tyr$^2$,Ser(OSO$_3$Na)$^7$]-Ac-CCK (2-8) | 0 | 40 |
| [Thr(OSO$_3$Na)$^7$]-Ac-CCK (2-8) | 166 | 0 |
| [Tyr$^2$,Thr(OSO$_3$Na)$^7$]-Ac-CCK (2-8) | 0 | 25 |
| [Hyp(OSO$_3$Na)$^7$]-Ac-CCK (2-8) | 300 | 0 |
| [D-Ala$^4$]-Ac-CCK (2-8) | 40 | 0 |

TABLE II

| | Delay until first tonic seizure (efficacy) | Delay until time of death (efficacy) |
| --- | --- | --- |
| CCK (1-8) | 100% | 100% |
| [Ser(OSO$_3$Na)$^7$]-Ac-CCK (2-8) | 60 | 120 |
| [Thr(OSO$_3$Na)$^7$]-Ac-CCK (2-8) | 140 | 120 |
| [Hyp(OSO$_3$Na)$^7$]-Ac-CCK (2-8) | 79 | 120 |
| [D-Ala$^4$]-Ac-CCK (2-8) | 100 | 126 |

The following peptides are similarly tested for CCK-activity and gastrinic activity and exhibit substantially no gastrinic activity while having CCK activity significantly greater than CCK(1-8):

[D—Ala$^4$, Hyp(OSO$_3$Na)$^7$]—Ac—CCK(2-8);

[Nle$^{3,6}$,D—Ala$^4$,Hyp(OSO$_3$Na)$^7$]—Suc—CCK(2-8);

[Nle$^{3,6}$,D—Ala$^4$,Hyp(OSO$_3$Na)$^7$]—Ac—CCK(2-8);

[Nle$^{3,6}$, Hyp(OSO$_3$Na)$^7$, Tyr(OCH$_3$)$^8$]—CCK(1-8); and

[Ser(OSO$_3$Na)$^1$, Nle$^{3,6}$, Hyp(OSO$_3$Na)$^7$]—CCK(1-8).

These and other similar CCK analogs, including the pharmaceutically acceptable salts thereof, may be combined with a pharmaceutically acceptable carrier to form a pharmaceutical composition which may be administered to animals, including humans, either intravenously, subcutaneously or parenterally. The administration may be employed by a physician to stimulate the contraction of the gall bladder and thus finds use as a diagnostic aid in the X-ray examination of the gall bladder. Particular of the analogs which do not exhibit the ability to stimulate gastrinic activity may be used to lower the secretion of gastric acid because of their property as serving as a physiological antagonist of gastrin. For such purposes, they may be administered either intravenously or subcutaneously to an animal species (e.g., cats or dogs) in a single dosage of about 0.3 to 1.0 ug./kg. of body weight. For this purpose, they may be administered parenterally by incorporating the appropriate dosage of the compound with carriers to form injectables according to standard pharmaceutical practice.

Likewise, various of the analogs have particular advantages in being used for their anticonvulsive effect, and comparison of the two Tables will show that the absence of the efficacy of these compounds to also stimulate the contraction of the gall bladder can be a further advantage in this respect. For administration to humans, these synthetic peptides should have a purity of at least about 90 percent, and preferably at least about 98 percent. This purity means the intended peptide constitutes the stated weight percent of all like peptides and peptide fragments present. For administration to other mammals, lower purities would be acceptable.

The CCK analogs having Tyr, Tyr(OCH$_3$) or des—NH$_2$—Tyr in the 0-, 1- or 8-positions can be iodinated with $^{125}$I which substitutes at the meta position of the phenol moiety. Treatment of the heptapeptide, octapeptide or nonapeptide is carried out with radioactive Na $^{125}$I and Chloramine-T as an oxidizing agent. The resultant peptide has the same biological potency as the uniodinated molecule but has the important advantage of being traceable throughout the body. It can also be used to measure the amount of CCK(1–8) in serum by RIA.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, additional natural amino acids could be added at the location of R$_0$ without substantially detracting from the biological potency of the agonist. Particular features of the invention are emphasized in the claims which follow.

What is claimed is:

1. A synthetic peptide having the formula: X—R$_0$—R$_1$—Tyr(Y)—R$_3$—R$_4$—Trp—R$_6$—R$_7$—R$_8$—NHQ wherein X is H, Suc, Ac, Oxa, Mal, Glt, Prp, Prl or Acr; R$_0$ is Gln, pGlu, Cys, Tyr, Tyr(OCH$_3$), des—NH$_2$—Tyr or desR$_0$; R$_1$ is Asp, Tyr(OH or SE), Ser(OH or SE), Hyp(OH or Se), Thr(OH or SE), Cys, Tyr(OCH$_3$) or desR$_1$; Y is OH or SE; R$_3$ is Met, Nva or Nle; R$_4$ is Gly, D—Cys or D—Ala; R$_6$ is Met, Nva or Nle; R$_7$ is Ser(SE), Thr(SE) or Hyp(SE); R$_8$ is Phe or Tyr(OCH$_3$); and Q is lower alkyl, fluoro lower alkyl or hydrogen; or a pharmaceutically acceptable salt thereof.

2. A synthetic peptide having the formula of claim 1 wherein X is Ac.

3. A synthetic peptide having the formula of claim 2 wherein Y is SE.

4. A synthetic peptide in accordance with claim 3 wherein R$_4$ is D—Ala.

5. A synthetic peptide having the formula of claim 4 wherein R$_0$ is desR$_0$, R$_1$ is desR$_1$, R$_7$ is Hyp(SE) and R$_8$ is Phe.

6. A synthetic peptide having the formula of claim 1 wherein R$_0$ is desR$_0$, R$_1$ is desR$_1$, R$_4$ is Gly and R$_8$ is Phe.

7. A synthetic peptide having the formula of claim 6 wherein R$_7$ is Ser(SE).

8. A synthetic peptide having the formula of claim 6 wherein R$_7$ is Thr(SE).

9. A synthetic peptide having the formula of claim 6 wherein R$_7$ is Hyp(SE).

10. A synthetic peptide in accordance with claim 8 wherein X is AC, R$_3$ and R$_6$ are Met and Y is OH.

11. A synthetic peptide in accordance with claim 9 wherein X is Ac, R$_3$ and R$_6$ are Met and Y is SE.

12. A synthetic peptide having the formula of claim 7 wherein X is Ac, R$_3$ and R$_6$ are Met and Y is SE.

13. A synthetic peptide having the formula of claim 8 wherein X is Ac, R$_3$ and R$_6$ are Met and Y is SE.

14. A synthetic peptide in accordance with claim 5 wherein R$_3$ and R$_6$ are Met.

15. A synthetic peptide in accordance with claim 1 wherein R$_8$ is Tyr(OCH$_3$).

16. A synthetic peptide in accordance with claim 15 wherein R$_3$ and R$_6$ are Nle.

17. A synthetic peptide having the formula of claim 16 wherein R$_0$ is desR$_0$, R$_1$ is desR$_1$, R$_4$ is Gly and R$_7$ is Tyr(SE), Ser(SE), Hyp(SE) or Thr(SE).

18. A synthetic peptide having the formula of claim 16 wherein R$_0$ is desR$_0$, R$_1$ is Asp, R$_4$ is Gly, R$_7$ is Hyp(OSO$_3$Na) and Y is SE.

19. A pharmaceutical composition for stimulating the contraction of the gall bladder containing an effective amount of the synthetic peptide of claim 13 or a pharmaceutically acceptable salt thereof, and a pharmaceutically acceptable liquid or solid carrier therefor.

20. A pharmaceutical composition for stimulating the contraction of the gall bladder containing an effective amount of the synthetic peptide of claim 12 or a pharmaceutically acceptable salt thereof and a pharmaceutically acceptable liquid or solid carrier therefor.

21. A pharmaceutical composition for stimulating the contraction of the gall bladder containing an effective amount of the synthetic peptide of claim 11 or a pharmaceutically acceptable salt thereof and a pharmaceutically acceptable liquid or solid carrier therefor.

22. A pharmaceutical composition for counteracting convulsions in a mammal containing an effective amount of the synthetic peptide of claim 13 or a pharmaceutically acceptable salt thereof, and a pharmaceutically acceptable carrier therefor.

23. A pharmaceutical composition for counteracting convulsions in a mammal containing an effective amount of the synthetic peptide of claim 14 or a pharmaceutically acceptable salt thereof, and a pharmaceutically acceptable carrier therefor.

24. A pharmaceutical composition for lowering the secretion of gastric acid comprising an effective amount of the peptide of claim 11 or a pharmaceutically acceptable salt thereof, and a pharmaceutically acceptable carrier therefor.

25. A pharmaceutical composition for lowering the secretion of gastric acid comprising an effective amount of the peptide of claim 12 or a pharmaceutically acceptable salt thereof, and a pharmaceutically acceptable carrier therefor.

26. A pharmaceutical composition for lowering the secretion of gastric acid comprising an effective amount of the peptide of claim 13 or a pharmaceutically acceptable salt thereof, and a pharmaceutically acceptable carrier therefor.

27. A pharmaceutical composition for lowering the secretion of gastric acid comprising an effective amount of the peptide of claim 14 or a pharmaceutically acceptable salt thereof, and a pharmaceutically acceptable carrier therefor.

28. A method for stimulating contraction of the gall bladder comprising administering an effective amount of the synthetic peptide having the formula: $X-R_0-R_1-Tyr(Y)-R_3-R_4-Trp-R_6-R_7-R_8-NHQ$
wherein X is H, Suc, Ac, Oxa, Mal, Glt, Prp, Prl or Acr; $R_0$ is Gln, pGlu, Cys, Tyr, Tyr(OCH$_3$), des—NH$_2$—Tyr or des$R_0$; $R_1$ is Asp, Tyr(OH or SE), Ser(OH or SE), Hyp(OH or SE), Thr(OH or SE), Cys, Tyr(OCH$_3$) or des$R_1$; Y is OH or SE; $R_3$ is Met, Nva or Nle; $R_4$ is D—Cys or D—Ala; $R_6$ is Met, Nva or Nle; $R_7$ is Asp, Ser(SE), Thr(SE) or Hyp(SE); $R_8$ is Phe or Tyr(OCH$_3$); and Q is lower alkyl, fluoro lower alkyl or hydrogen; provided that either Y is SE or $R_7$ is other than Asp; or a pharmaceutically acceptable salt thereof.

29. A method according to claim 28 wherein $R_4$ is D—Ala.

30. A method of counteracting convulsions in an animal comprising administering an effective amount of a synthetic peptide having the formula: $X-R_0-R_1-Tyr(Y)-R_3-R_4-Trp-R_6-R_7-R_8-NHQ$
wherein X is H, Suc, Ac, Oxa, Mal, Glt, Prp, Prl or Acr; $R_0$ is Gln, pGlu, Cys, Tyr, Tyr(OCH$_3$), des—NH$_2$—Tyr or des$R_0$; $R_1$ is Asp, Tyr(OH or SE), Ser(OH or SE), Hyp(OH or SE), Thr(OH or SE), Cys, Tyr(OCH$_3$) or des$R_1$; Y is OH or SE; $R_3$ is Met, Nva or Nle; $R_4$ is D—cys or D—Ala; $R_6$ is Met, Nva or Nle; $R_7$ is Asp, Ser(SE), Thr(SE) or Hyp(SE); $R_8$ is Phe or Tyr(OCH$_3$); and Q is lower alkyl, fluoro lower alkyl or hydrogen; provided that either Y is SE or $R_7$ is other than Asp; or a pharmaceutically acceptable salt thereof.

31. A method according to claim 30 wherein $R_4$ is D—Ala.

* * * * *